United States Patent
Okamura et al.

(10) Patent No.: US 6,686,343 B1
(45) Date of Patent: Feb. 3, 2004

(54) TRIAZOLOPURINE DERIVATIVES, PHARMACEUTICAL COMPOSITIONS CONTAINING THE DERIVATIVES, AND ADENOSINE A3 RECEPTOR AFFINITIVE AGENTS

(75) Inventors: Takashi Okamura, Tokushima (JP); Yasuhisa Kurogi, Tokushima (JP); Hiroshi Nishikawa, Tokushima (JP)

(73) Assignee: Otsuka Pharmaceutical Factory, Inc., Tokushima (JP)

(*) Notice: Subject to any disclaimer, the term of this patent is extended or adjusted under 35 U.S.C. 154(b) by 0 days.

(21) Appl. No.: 10/089,244

(22) PCT Filed: Sep. 22, 2000

(86) PCT No.: PCT/JP00/06487
§ 371 (c)(1),
(2), (4) Date: Mar. 28, 2002

(87) PCT Pub. No.: WO01/23391
PCT Pub. Date: Apr. 5, 2001

(30) Foreign Application Priority Data

Sep. 28, 1999 (JP) .................................. 11-275270
May 29, 2000 (JP) ..................................... 2000-157655

(51) Int. Cl.$^7$ .................... C07D 487/14; A61K 31/519; A61P 11/06; A61P 9/06; A61P 37/08
(52) U.S. Cl. ................. 514/81; 514/267; 544/244; 544/251
(58) Field of Search ................. 544/251, 244; 514/81, 267

(56) References Cited

U.S. PATENT DOCUMENTS 5,935,964 A * 8/1999 Baraldi et al. ............... 514/267
6,288,070 B1 9/2001 Okamura et al.

FOREIGN PATENT DOCUMENTS

| DE | 26 18 122 | 11/1977 |
| EP | 0 133 505 | 2/1985 |
| EP | 0 263 071 | 4/1988 |
| EP | 425 000 | 5/1991 |
| EP | 0 429 933 | 6/1991 |
| EP | 0 476 744 | 3/1992 |
| EP | 0 884 318 | 12/1998 |
| EP | 1 069 126 A1 | 1/2001 |

OTHER PUBLICATIONS

F. Gatta, et al., "Synthesis of 2,8–Disubstituted 1,2, 4–Triazol[5, 1–I]purines" Journal of Heterocyclic Chemistry, Hetero Corp., Tampa, Fl. US (vol. 31, 1994, pp. 1171–1176, XP002921239).

F. Gatta et al., "Synthesis of imidazo [1,2–c]pyrazolo[4,3–e] pyrimidines, pyrazol[4,3–e]1,2,4–triazolo[1,5–I]purines: new potent adenosine $A_2$ receptor antagonists" European Journal of Medicinal Chemistry, Editions Scientifique Elsevier, Paris, Fr., (vol. 28, No. 7/8, 1993, pp. 569–576, XP009002008).

T. Okamura, et al. "1,2,4–Triazolo[5,1–i]purine Derivatices as Highly Potent and Selective Human Adenosine $A_3$ Receptor Ligands" Journal of Medicinal Chemistry, American Chemical Society. Washington, US. (vol. 45, No. 17, Jul. 16, 2002 pp. 3703–3708, XP002222673).

* cited by examiner

*Primary Examiner*—Mark L. Berch
(74) *Attorney, Agent, or Firm*—Sughrue Mion, PLLC

(57) ABSTRACT

Disclosed is triazolopurine derivatives represented by the general formula (I):

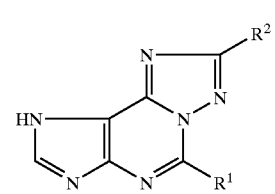

(1)

wherein $R^1$ and $R^2$ are as defined in the description. This compounds exhibit affinity for adenosine A3 receptor and are therefore useful as the ingredient of pharmaceutical compositions.

8 Claims, No Drawings

TRIAZOLOPURINE DERIVATIVES, PHARMACEUTICAL COMPOSITIONS CONTAINING THE DERIVATIVES, AND ADENOSINE A3 RECEPTOR AFFINITIVE AGENTS

TECHNICAL FIELD

The present invention relates to a novel triazolopurine derivative which exhibits an adenosine A3 receptor affinity, a pharmaceutical composition containing the derivative, and an adenosine A3 receptor affinitive agent.

BACKGROUND ART

J. Heterocyclic Chem., 31, 1171 (1994) disclosed that 2-aryl-8-fluorobenzyl-1,2,4-triazolo[5,1-i]purine is useful as an adenosine A2 receptor antagonist.

An object of the present invention is to provide a novel compound which has an affinity to an adenosine A3 receptor.

DISCLOSURE OF THE INVENTION

The triazolopurine derivative of the present invention is represented by the general formula (1):

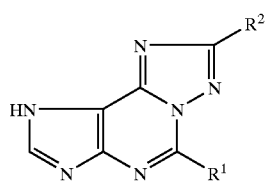

(1)

wherein $R^1$ represents a lower alkoxy lower alkyl group, a lower alkylsulfinyl lower alkyl group, a lower alkylsulfonyl lower alkyl group, a lower alkoxycarbonyl lower alkyl group, a carboxy lower alkyl group, a cycloalkyl group, a halogen-substituted lower alkyl group, a phosphono lower alkyl group, a lower alkylphosphono lower alkyl group, a di-lower alkylphosphono lower alkyl group, a lower alkanoyloxy lower alkyl group, a hydroxy lower alkyl group, a di-lower alkylamino lower alkyl group, a phenyl lower alkoxy lower alkyl group, or a lower alkylthio lower alkyl group; $R^2$ represents a phenyl group which may have, as a substituent, 1 to 3 groups selected from the group consisting of lower alkyl group, lower alkoxy group, halogen atom, halogen-substituted lower alkyl group, and phenyl group.

The triazolopurine derivative of the present invention is a novel compound which has never been described in reference documents.

In the present invention, $R^1$ is preferably a lower alkoxy lower alkyl group, a lower alkylthio lower alkyl group, a lower alkylsulfinyl lower alkyl group, a lower alkylsulfonyl lower alkyl group, or a carboxyl lower alkyl group.

$R^1$ is more preferably a methoxymethyl group, an ethoxymethyl group, a 2-methoxyethyl group, a 2-methylsulfinylethyl group, a 2-methylsulfonylethyl group, a 2-carboxyethyl group, a 3-carboxypropyl group, a 4-carboxybutyl group, or a 2-methylthioethyl group.

$R^2$ is preferably a phenyl group, a 4-biphenylyl group, a 4-n-propoxyphenyl group, a 4-t-butylphenyl group, a 4-chlorophenyl group, a 4-trifluoromethylphenyl group, or a 3,4,5-trimethoxyphenyl group.

It is expected that the triazolopurine derivative of the present invention is applied to antihypertensive agent, antiallergic agent, anti-inflammatory agent, remedy for ischemic disease, remedy for leukemia, antipruritic agent, expectorants, antitussives, remedy for asthma, and analgesic, as a compound capable of binding with an adenosine A3 receptor, because of its excellent affinity to an adenosine A3 receptor.

Accordingly, the present invention also provides a pharmaceutical composition comprising the triazolopurine derivative described above and a pharmaceutically acceptable carrier.

Specifically, the present invention provides an adenosine A3 receptor affinitive agent comprising the triazolopurine derivative described above as an active ingredient.

BEST MODE FOR CARRYING OUT THE INVENTION

In the present invention, the lower alkyl group includes, for example, straight-chain or branched lower alkyl groups having 1 to 6 carbon atoms, such as methyl, ethyl, propyl, butyl, isobutyl, tert-butyl, pentyl, hexyl, isopropyl, isopentyl, neopentyl, and 1-ethylpropyl.

The lower alkoxy group includes, for example, straight-chain or branched lower alkoxy groups having 1 to 6 carbon atoms, such as methoxy, ethoxy, propoxy, butoxy, tert-butoxy, pentyloxy, and hexyloxy.

The lower alkoxy lower alkyl group includes, for example, lower alkoxy lower alkyl groups wherein both the alkoxy moiety and the alkyl moiety have 1 to 6 carbon atoms, such as methoxymethyl, ethoxymethyl, propoxymethyl, butoxymethyl, t-butoxymethyl, pentyloxymethyl, hexyloxymethyl, 1-methoxyethyl, 2-methoxyethyl, 3-methoxypropyl, 4-methoxybutyl, 5-methoxypentyl, 6-methoxyhexyl, 2-ethoxyethyl, and 3-propoxypropyl.

The lower alkylsulfinyl lower alkyl group includes, for example, lower alkylsulfinyl lower alkyl groups wherein the alkyl moiety has 1 to 6 carbon atoms, such as methylsulfinylmethyl, ethylsulfinylmethyl, propylsulfinylmethyl, butylsulfinylmethyl, t-butylsulfinylmethyl, pentylsulfinylmethyl, hexylsulfinylmethyl, 1-methylsulfinylethyl, 2-methylsulfinylethyl, 3-methylsulfinylpropyl, 4-methylsulfinylbutyl, 5-methylsulfinylpentyl, and 6-methylsulfinylhexyl.

The lower alkylsulfonyl lower alkyl group includes, for example, lower alkylsulfonyl lower alkyl groups wherein the alkyl moiety has 1 to 6 carbon atoms, such as methylsulfonylmethyl, ethylsulfonylmethyl, propylsulfonylmethyl, butylsulfonylmethyl, t-butylsulfonylmethyl, pentylsulfonylmethyl, hexylsulfonylmethyl, 1-methylsulfonylethyl, 2-methylsulfonylethyl, 3-methylsulfonylpropyl, 4-methylsulfonylbutyl, 5-methylsulfonylpentyl, and 6-methylsulfonylhexyl.

The lower alkoxycarbonyl lower alkyl group includes, for example, lower alkoxycarbonyl lower alkyl groups wherein both the alkoxy moiety and the alkyl moiety have 1 to 6 carbon atoms, such as methoxycarbonylmethyl, ethoxycarbonylmethyl, propoxycarbonylmethyl, butoxycarbonylmethyl, pentyloxycarbonylmethyl, hexyloxycarbonylmethyl, 1-methoxycarbonylethyl, 2-methoxycarbonylethyl, 3-methoxycarbonylpropyl, 4-methoxycarbonylbutyl, 5-methoxycarbonylpentyl, 6-methoxycarbonylhexyl, 2-ethoxycarbonylethyl, 3-ethoxycarbonylpropyl, and 4-ethoxycarbonylbutyl.

The carboxy lower alkyl group includes, for example, carboxy lower alkyl groups wherein the alkyl moiety has 1 to 6 carbon atoms, such as carboxymethyl, 1-carboxyethyl, 2-carboxyethyl, 3-carboxypropyl, 4-carboxybutyl, 5-carboxypentyl, and 6-carboxyhexyl.

The lower alkylthio lower alkyl group includes, for examples, lower alkylthio lower alkyl groups wherein the alkyl moiety has 1 to 6 carbon atoms, such as methylthiomethyl, ethylthiomethyl, propylthiomethyl, butylthiomethyl, t-butylthiomethyl, pentylthiomethyl, hexylthiomethyl, 1-methylthioethyl, 2-methylthioethyl, 3-methylthiopropyl, 4-methylthiobutyl, 5-methylthiopentyl, 6-methylthiohexyl, 2-ethylthioethyl, and 3-propylthiopropyl.

The halogen-substituted lower alkyl group includes, for example, perfluoro lower alkyl groups wherein the alkyl moiety has 1 to 6 carbon atoms, such as trifluoromethyl, pentafluoroethyl, heptafluoropropyl, nonafluorobutyl, undecafluoropentyl, and tridecafluorohexyl.

The cycloalkyl group includes, for example, cycloalkyl groups having 3 to 8 carbon atoms, such as cyclopropyl, cyclobutyl, cyclopentyl, cyclohexyl, cycloheptyl, and cyclooctyl.

The phosphono lower alkyl group includes, for example, phosphono lower alkyl groups wherein the alkyl moiety has 1 to 6 carbon atoms, such as phosphonomethyl, 1-phosphonoethyl, 2-phosphonoethyl, 3-phosphonopropyl, 4-phosphonobutyl, 5-phosphonopentyl, and 6-phosphonohexyl.

The lower alkylphosphono lower alkyl group includes, for example, lower alkylphosphono lower alkyl groups wherein the alkyl moiety has 1 to 6 carbon atoms, such as methylphosphonomethyl, ethylphosphonomethyl, propylphosphonomethyl, butylphosphonomethyl, pentylphosphonomethyl, hexylphosphonomethyl, 2-ethylphosphonoethyl, 1-ethylphosphonoethyl, 3-ethylphosphonopropyl, 4-ethylphosphonobutyl, 5-ethylphosphonopentyl, and 6-ethylphosphonohexyl.

The di-lower alkylphosphono lower alkyl group includes, for example, di-lower alkylphosphono lower alkyl groups wherein the alkyl moiety has 1 to 6 carbon atoms, such as dimethylphosphonomethyl, diethylphosphonomethyl, dipropylphosphonomethyl, dibutylphosphonomethyl, dipentylphosphonomethyl, dihexylphosphonomethyl, ethylmethylphosphonomethyl, 2-diethylphosphonoethyl, 1-diethylphosphonoethyl, 3-diethylphosphonopropyl, 4-diethylphosphonobutyl, 5-diethylphosphonopentyl, and 6-diethylphosphonohexyl.

The lower alkanoyloxy lower alkyl group includes, for example, lower alkanoyloxy lower alkyl groups wherein both the alkanoyl moiety and the alkyl moiety have 1 to 6 carbon atoms, such as acetoxymethyl, propionyloxymethyl, butyryloxymethyl, valeryloxymethyl, hexanoyloxymethyl, heptanoyloxymethyl, 1-acetoxyethyl, 2-acetoxyethyl, 3-acetoxypropyl, 4-acetoxybutyl, 5-acetoxypentyl, and 6-acetoxyhexyl.

The hydroxy lower alkyl group includes, for example, hydroxy lower alkyl groups wherein the alkyl moiety has 1 to 6 carbon atoms, such as hydroxymethyl, 2-hydroxyethyl, 1-hydroxyethyl, 3-hydroxypropyl, 4-hydroxybutyl, 5-hydroxypentyl, and 6-hydroxyhexyl.

The di-lower alkylamino lower alkyl group includes, for example, di-lower alkylamino lower alkyl groups wherein the alkyl moiety has 1 to 6 carbon atoms, such as dimethylaminomethyl, diethylaminomethyl, dipropylaminomethyl, dibutylaminomethyl, dipentylaminomethyl, dihexylaminomethyl, ethylmethylaminomethyl, 2-dimethylaminoethyl, 1-dimethylaminoethyl, 3-dimethylaminopropyl, 4-dimethylaminobutyl, 5-dimethylaminopentyl, and 6-dimethylaminohexyl.

The phenyl lower alkoxy lower alkyl group includes, for example, phenyl lower alkoxy lower alkyl groups wherein both the alkoxy moiety and the alkyl moiety have 1 to 6 carbon atoms, such as benzyloxymethyl, 2-phenylethoxymethyl, 3-phenylpropoxymethyl, 4-phenylbutoxymethyl, 5phenylpentyloxymethyl, 6-phenylhexyloxymethyl, 1-benzyloxyethyl, 2-benzyloxyethyl, 3-benzyloxypropyl, 4-benzyloxybutyl, 5-benzyloxypentyl, and 6-benzyloxyhexyl.

The phenyl group which optionally has a group selected from lower alkyl group, lower alkoxy group, halogen atom, halogen-substituted lower alkyl group, and phenyl group as a substituent includes, for example, phenyl groups which optionally have 1 to 3 substituents, such as 2-methylphenyl, 3-methylphenyl, 4-methylphenyl, 4-ethylphenyl, 4-propylphenyl, 4-isopropylphenyl, 4-butylphenyl, 4-t-butylphenyl, 4-pentylphenyl, 4-hexylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 3,4-diethylphenyl, 3,4-dipropylphenyl, 3,4-dibutylphenyl, 3,4-dipentylphenyl, 3,4-dihexylphenyl, 3,4,5-trimethylphenyl, 2,3,4-trimethylphenyl, 2,3,5-trimethylphenyl, 2,3,6-trimethylphenyl, 2,4,6-trimethylphenyl, 2,4,5-trimethylphenyl, 3,4,5-triethylphenyl, 3,4,5-tripropylphenyl, 3,4,5-tributylphenyl, 3,4,5-tripentylphenyl, 3,4,5-trihexylphenyl, 2-methoxyphenyl, 3-methoxyphenyl, 4-methoxyphenyl, 4-ethoxyphenyl, 4-propoxyphenyl, 4-butoxyphenyl, 4-pentyloxyphenyl, 4-hexyloxyphenyl, 2,3-dimethoxyphenyl, 2,4-dimethoxyphenyl, 2,5-dimethoxyphenyl, 2,6-dimethoxyphenyl, 3,4-dimethoxyphenyl, 3,5-dimethoxyphenyl, 3,4-diethoxyphenyl, 3,4-dipropoxyphenyl, 3,4-dibutoxyphenyl, 3,4-dipentyloxyphenyl, 3,4-dihexyloxyphenyl, 3,4,5-trimethoxyphenyl, 2,3,4-trimethoxyphenyl, 2,3,5-trimethoxyphenyl, 2,3,6-trimethoxyphenyl, 2,4,6-trimethoxyphenyl, 2,4,5-trimethoxyphenyl, 3,4,5-triethoxyphenyl, 3,4,5-tripropoxyphenyl, 3,4,5-tributoxyphenyl, 3,4,5-tripentyloxyphenyl, 3,4,5-trihexyloxyphenyl, 4-methoxy-3-methylphenyl, 4-methoxy-2-methylphenyl, 3-methoxy-2-methylphenyl, 4-methoxy-3,5-dimethylphenyl, 4-biphenylyl, 3-biphenylyl, 2-biphenylyl, 2-trifluoromethylphenyl, 3-trifluoromethylphenyl, 4-trifluoromethylphenyl, 4-pentafluoroethylphenyl, 4-heptafluoropropylphenyl, 4-nonafluorobutylphenyl, 4-undecafluoropentylphenyl, 4-tridecafluorohexylphenyl, 2,4-bis(trifluoromethyl)phenyl, 3,5-bis(trifluoromethyl)phenyl, 2,4,6-tris(trifluoromethyl) phenyl, 2-chlorophenyl, 3-chlorophenyl, 4-chlorophenyl, 4-fluorophenyl, 4-bromophenyl, 4-iodophenyl, 2,4-dichlorophenyl, 3,4-dichlorophenyl, 3,5-dichlorophenyl, 2,4,6-trichlorophenyl group, in addition to phenyl group. All of the lower alkyl group, the lower alkoxy group, and the halogen-substituted lower alkyl group are groups having 1 to 6 carbon atoms.

The compound (1) of the present invention can be prepared by the reaction scheme-1 to reaction scheme-6.

[Reaction Scheme-1]

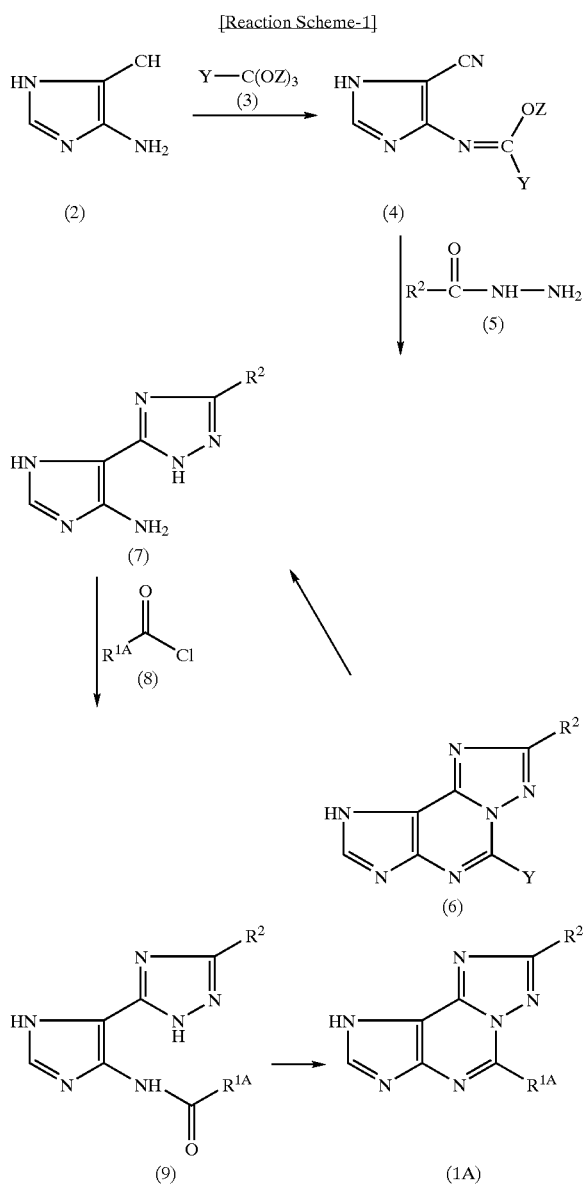

wherein $R^{1A}$ represents a lower alkoxy lower alkyl group, a lower alkoxycarbonyl lower alkyl group, a cycloalkyl group, a halogen-substituted lower alkyl group, a di-lower alkylphosphono lower alkyl group, a lower alkanoyloxy lower alkyl group, a di-lower alkylamino lower alkyl group, a phenyl lower alkoxy lower alkyl group, or a lower alkylthio lower alkyl group; $R^2$ is as defined above; and Y and Z are the same or different and represent a lower alkyl group.

First, a compound represented by the formula (2) is reacted with an orthoester derivative represented by the formula (3) to obtain an imino ester derivative represented by the formula (4). This reaction is carried out by adding the orthoester derivative (3) in an equimolar amount or more relative to the amount of the compound (2) and heating at a temperature within a range from 50° C. to reflux temperature for about 10 minutes to 5 hours in the absence of a solvent, or in an inert solvent. As the inert solvent, for example, N,N-dimethylformamide (DMF), N,N-dimethylacetamide (DMA), dimethyl sulfoxide (DMSO), methanol, diphenyl ether, xylene, and diethylene glycol dimethyl ether can be used.

The resulting imino ester derivative (4) is reacted with an acyl hydrazine derivative represented by the formula (5), after the ester derivative is purified according to a conventional method or not, to obtain the compound (6). This reaction is carried out by adding the acyl hydrazine derivative (5) in an equimolar amount or slightly more relative to the amount of the imino ester derivative (4) in an inert solvent, optionally adding a catalytic amount of 1,8-diazabicyclo[5,4,0]-7-undecene and heating at a temperature within a range from 50° C. to reflux temperature for about 1 to 50 hours. The inert solvent includes the same solvents as those described above. If necessary, the reaction solution may be alkalified by adding an aqueous sodium hydroxide solution and an aqueous potassium hydroxide solution and reacted furthermore at a temperature within a range from 0° C. to room temperature for about 10 minutes to 50 hours after the completion of the heating reaction.

Then, the compound (6) is converted into an amine compound (7) by refluxing in an aqueous solution of mineral acid such as hydrochloric acid or sulfuric acid for 5 minutes to 50 hours.

Then, the amine compound (7) is acylated. This acylation can be carried out by reacting the amine compound (7) with a carboxylic acid chloride (8) in an amine-based inert solvent such as pyridine, lutidine, triethylamine, or 4-(N,N-dimethylamino)pyridine. In this reaction, the carboxylic acid chloride (8) is used in an equimolar amount or more and the reaction is completed within about 10 minutes to 3 hours at a temperature within a range from 0° C. to reflux temperature. Since a compound substituted with a plurality of acyl groups may be included sometime in the acylation reaction, the inclusion can optionally be converted into the objective monoacyl compound (9) by refluxing the product, together with a catalytic amount of an alkaline such as anhydrous potassium carbonate or anhydrous sodium carbonate, in an inert solvent such as methanol or ethanol for about 10 minutes to 2 hours.

Subsequently, the monoacyl compound (9) thus obtained is converted into a compound (1A) of the present invention by the cyclization reaction. The cyclization reaction is carried out by reacting the monoacyl compound (9) with a halogenated trialkylsilane in an inert solvent in the presence of a base.

As the inert solvent, for example, aromatic and aliphatic hydrocarbons such as benzene, toluene, xylene, and petroleum ether; ethers such as diethyl ether and tetrahydrofuran; halogenated hydrocarbons such as dichloromethane, chloroform, carbon tetrachloride, and 1,2-dichloroethane; and aliphatic nitriles such as acetonitrile can be used. As the base, for example, tertiary amine such as triethylamine, diisopropylethylamine, N,N-diethylaniline, N-methyl morpholine, pyridine, or 4-(N,N-dimethylamino)pyridine can be preferably used. As the halogenated trialkylsilane, for example, chlorotrialkylsilane such as chlorotrimethylsilane, chlorotriethylsilane, chloroethyldimethylsilane, chlorodimethylpropylsilane, chlorobutyldimethylsilane, chlorotripropylsilane, tributylchlorosilane, or chloroethylmethylpropylsilane can be preferably used.

The amount of the halogenated trialkylsilane and base to be used is not specifically limited, but is generally controlled to an equal equivalent weight or more, and preferably from 3- to 20-fold equivalent weight relative to the amount of the monoacyl compound (9). The cyclization reaction is usually completed within about 0.5 to 100 hours at a temperature within a range from 0 to 100° C.

[Reaction Scheme-2]

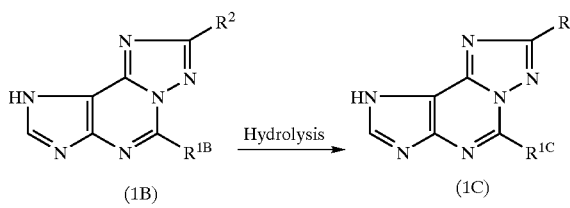

wherein $R^{1B}$ represents a lower alkoxycarbonyl lower alkyl group; $R^{1C}$ represents a carboxy lower alkyl group; and $R^2$ is as defined above.

As shown in the reaction scheme-2, a compound (1B) of the present invention is converted into a compound (1C) of the present invention by the hydrolysis reaction. The reaction is carried out by treating with an alkali such as aqueous sodium hydroxide solution or aqueous potassium hydroxide solution, in an inert solvent such as methanol or ethanol. The amount of the alkali to be used is preferably controlled to an equal equivalent weight or more relative to the amount of the compound (1B). The reaction is completed within about 0.5 to 10 hours at a temperature within a range from 0° C. to about room temperature.

[Reaction Scheme-3]

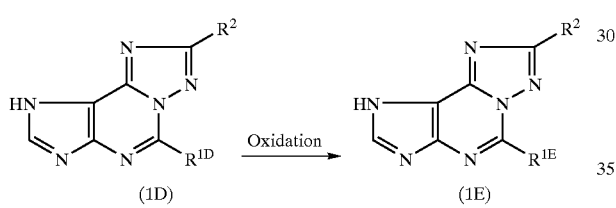

wherein $R^{1D}$ represents a lower alkylthio lower alkyl group; $R^{1E}$ represents a lower alkylsulfinyl lower alkyl group or a lower alkylsulfonyl lower alkyl group; and $R^2$ is as defined above.

As shown in the reaction scheme-3, a compound (1D) of the present invention is converted into a compound (1E) of the present invention by the oxidization reaction. The oxidization reaction is carried out by using hydrogen peroxide as an oxidizing agent in acetic acid, or using m-chloroperbenzoic acid or sodium periodate as an oxidizing agent in an inert solvent such as dichloromethane or carbon tetrachloride. In case the oxidization reaction is carried out until the sulfinyl compound is obtained, the amount of the oxidizing agent to be used is controlled to an equal equivalent weight or slightly more relative to the raw compound and the reaction is carried out at a temperature within a range from 0° C. to about room temperature for about 15 minutes to 10 hours. In case the oxidization reaction is carried out until the sulfonyl compound is obtained, the amount of the oxidizing agent to be used is controlled to a 2-fold equivalent weight or more relative to the raw compound and, if necessary, a catalyst such as sodium tungstate is added and, moreover, the reaction is carried out at a temperature within a range from 0° C. to about reflux temperature for about 15 minutes to 10 hours.

The sulfonyl compound can also be obtained by subjecting the resulting sulfinyl compound to the oxidization reaction again. The conditions to be employed may be either of two conditions described above.

[Reaction Scheme-4]

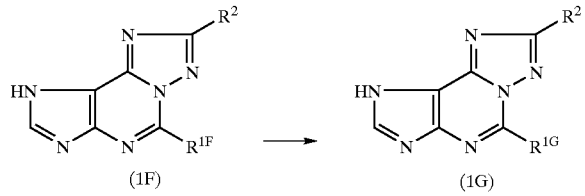

wherein $R^{1F}$ represents a di-lower alkylphosphono lower alkyl group; $R^{1G}$ represents a lower alkylphosphono lower alkyl group; and $R^2$ is as defined above.

According to the reaction scheme-4, the objective compound (1G) can be obtained by reacting a compound (1F) with a halogenated lithium such as lithium chloride, lithium bromide or lithium iodide and treating the resulting compound with an aqueous solution of mineral acid such as hydrochloric acid or sulfuric acid at a stage of post-treatment. The reaction is carried out by using an excess amount of the halogenated lithium in an inert solvent such as acetonitrile or DMF at a temperature within a range from room temperature to reflux temperature of the solvent for 5 to 24 hours.

[Reaction Scheme-5]

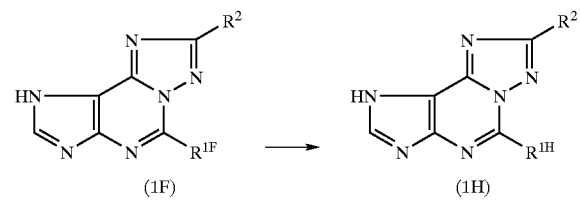

wherein $R^{1H}$ represents a phosphono lower alkyl group; and $R^{1F}$ and $R^2$ are as defined above.

According to the reaction scheme-5, the objective compound (1H) can be obtained by reacting a compound (1F) with a halogenated trialkylsilane such as chlorotrimethylsilane or chlorotriethylsilane and treating the resulting compound with an aqueous solution of mineral acid such as hydrochloric acid or sulfuric acid at a stage of post-treatment. The reaction is carried out in an inert solvent such as acetonitrile or propionitrile in the presence of an alkaline metal iodide salt such as sodium iodide or potassium iodide. The amount of the halogenated trialkylsilane and alkaline metal iodide salt to be used is controlled to a 2-fold equivalent weight or more relative to the compound (1F) and the reaction is completed within about 2 to 12 hours at a temperature within a range from room temperature to reflux temperature of the solvent.

[Reaction Scheme-6]

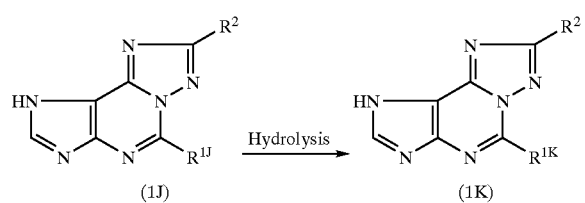

wherein $R^{1J}$ represents a lower alkanoyloxy lower alkyl group; $R^{1K}$ represents a hydroxy lower alkyl group; and $R^2$ is as defined above.

According to the reaction scheme-6, a compound (1J) can be converted into the objective compound (1K) by hydrolysis. The hydrolysis reaction can be carried out by employing the same conditions as those in the hydrolysis reaction of the reaction scheme-2.

The objective compound in each process of the reaction scheme can be easily isolated and purified by a conventional separation means. The separation means includes adsorption chromatography, preparative thin-layer chromatography, recrystallization, solvent extraction or the like.

Among the compounds (1) of the present invention prepared as described above, it is considered that the compound includes the following four structural formulas as a tautomer and the compounds (1) can be represented by any of the structural formulas:

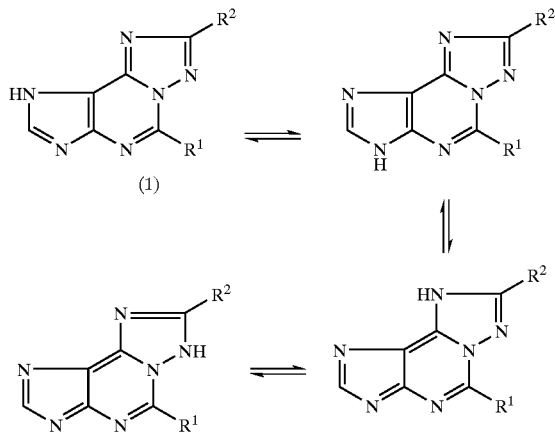

wherein $R^1$ and $R^2$ are as defined above.

The compounds (1) of the present invention can be formed into pharmaceutically acceptable acid addition salts, and these salts are also included in the present invention. The acid capable of forming these acid addition salts includes, for example, inorganic acids such as hydrochloric acid, hydrobromic acid, and sulfuric acid; and organic acids such as oxalic acid, fumaric acid, maleic acid, tartaric acid, citric acid, and p-toluenesulfonic acid. The acid addition salts can be formed by a conventional method.

The compounds (1) of the present invention can be formed into alkaline metal salts such as sodium salt and potassium salt; alkaline earth metal salts such as calcium salt and magnesium salt; and copper salts, and these salts can also be included in the present invention.

The compounds (1) of the present invention are used in the form of a general pharmaceutical preparation by using, together with a suitable non-toxic preparation carrier. The preparation carrier include diluents and excipients, such as fillers, extenders, binders, humectants, disintegrators, surfactants, and lubricants, which are usually used according to the form of the preparation, and these are appropriately selected and used according to the unit dosage form of the resulting preparation.

As the unit dosage form of the pharmaceutical preparation using the compound (1), various forms can be selected according to the therapeutic purposes and typical examples thereof include tablets, pills, powders, liquid preparations, suspensions, emulsions, granules, capsules, suppositories, injections (e.g. liquid preparations, suspensions, etc.), and ointments.

In case of forming into the form of tablets, there can be used, as the preparation carrier, excipients such as lactose, sucrose, sodium chloride, glucose, urea, starch, calcium carbonate, kaolin, crystalline cellulose, silicic acid, and potassium phosphate; binders such as water, ethanol, propanol, simple syrup, glucose solution, starch solution, gelatin solution, carboxymethylcellulose, hydroxypropylcellulose, methylcellulose, and polyvinyl pyrrolidone; disintegrators such as sodium carboxymethylcellulose, calcium carboxymethylcellulose, low substituted hydroxypropylcellulose, dried starch, sodium alginate, agar powder, laminaran powder, sodium hydrogencarbonate, and calcium carbonate; surfactants such as polyoxyethylene sorbitan fatty acid esters, sodium lauryl sulfate, and stearic acid monoglyceride; disintegration inhibitors such as sucrose, stearin, cacao butter, and hydrogenated oil; absorption accelerators such as quaternary ammonium base and sodium lauryl sulfate; humectants such as glycerin and starch; adsorbents such as starch, lactose, kaolin, bentonite, and colloidal silicic acid; and lubricants such as purified talc, stearate, powdered boric acid, and polyethylene glycol.

If necessary, tablets can be formed into tablets coated with a common coating, for example, sugar-coated tablets, gelatin-coated tablets, enteric coated tablets, film coating tablets, double layered tablets, or mutilayer tablets.

In case of forming into the form of pills, there can be used, as the preparation carrier, excipients such as glucose, lactose, starch, cacao butter, hardened vegetable oil, kaolin, and talc; binders such as gum arabic, powdered tragacanth, gelatin, and ethanol; and disintegrators such as laminaran and agar.

In case of forming into the form of suppositories, there can be used, as the preparation carrier, polyethylene glycol, cacao butter, higher alcohol, esters of higher alcohol, gelatin, and semisynthetic glyceride.

Capsules are usually prepared by mixing the compound (1) of the present invention with various preparation carriers mentioned above and filling a hard gelatin capsule or a soft capsule with the mixture.

In case of preparing as injections such as liquid preparations, emulsions or suspension, these are preferably sterilized and are isotonic with blood. In case of forming into the form of injections, there can be used, as the diluent, water, ethyl alcohol, macrogol, propylene glycol, ethoxylated isostearyl alcohol, polyoxylated isostearyl alcohol, or polyoxyethylene sorbitan fatty acid esters. In this case, salt, glucose or glycerin may be contained in an enough amount to prepare an isotonic solution and common solubilizers, buffer agents or soothing agents may also be added.

If necessary, the pharmaceutical preparation further contains colorants, preservatives, perfumes, flavors, sweeteners, or other drugs.

In case of forming into the form such as paste, cream, or gel, there can be used, as the diluent, white vaseline, paraffin, glycerin, cellulose derivative, polyethylene glycol, silicon, and bentonite.

The amount of the compound (1) of the present invention to be incorporated in the pharmaceutical preparation is not specifically limited and appropriately selected from a wide range, but is preferably within a range from about 1 to 85% by weight based on the pharmaceutical preparation.

The administration method of the pharmaceutical preparation is not specifically limited, but is appropriately decided according to the form of preparations, age of patients, sex and other conditions, or conditions of diseases. For example, tablets, pills, liquid preparations, suspensions, emulsions, granules and capsules are orally administered, while injections are intravenously administered alone or in combination with a conventional fluid such as glucose or amino acid, or intramuscularly, intracutaneously, subcutaneously or intraperitoneally administered alone, if necessary. Furthermore, suppositories are intrarectally administered.

The dose of the pharmaceutical preparation varies depending on the administration method, age of patients, sex and other conditions, or conditions of diseases, but a dairy dose of the compound (1) of the present invention is usually within a range from about 0.5 to 20 mg/kg-weight, and preferably from about 1 to 10 mg/kg-weight. The pharmaceutical preparation can be administered 1 to 4 times per day.

INDUSTRIAL APPLICABILITY

It is expected that the triazolopurine derivative of the present invention is applied to antihypertensive agent, antiallergic agent, anti-inflammatory agent, remedy for ischemic disease, remedy for leukemia, antipruritic agent, expectorants, antitassives, remedy for asthma, and analgesic because of its affinity to an adenosine A3 receptor.

EXAMPLES

The following Reference Examples and Examples further illustrate the compounds of the present invention in detail.

Reference Example 1

Preparation of 5-methyl-8-phenyl-1H-1,2,4-triazolo[5,1-i]purine 5 g of 4-amino-5-cyanoimidazole was suspended in 10 mL of DMF and 10 mL of trimethyl orthoacetate was added, followed by stirring at 90° C. for 30 minutes. The reaction solution was concentrated under reduced pressure and the residue was diluted with ethyl acetate, and then 4.2 g the deposited crystal was collected by filtration. The mother solution was concentrated and the residue was purified by silica gel column chromatography (eluent: ethyl acetate), recrystallized from ethyl acetate-n-hexane, and then the resulting crystal was combined with 4.2 g of the crystal described above to obtain 7.1 g of methyl N-(5-cyanoimidazole-4-yl)acetoimidate as a crystal (melting point: 147–149° C.).

4.0 g of methyl N-(5-cyanoimidazol-4-yl)acetoimidate thus obtained and 3.65 g of N-benzoylhydrazine were dissolved in 40 ml of DMF, followed by stirring at 80° C. for one hour and further stirring at 150° C. for 15 hours. After the reaction solution was air-cooled to room temperature, the pH was adjusted within a range from 9 to 10 by adding dropwise 13 ml of an aqueous 10% sodium hydroxide solution and the solution was stirred at room temperature for one hour. After the completion of the reaction, the pH was adjusted to 3 by sequentially adding 10% hydrochloric acid and water. The deposited crystal was collected by filtration and washed with hot ethanol to obtain 5.5 g of the objective compound as a crystal. (Melting point: 285° C. or higher)

Reference Examples 2 to 7

In the same manner as in Reference Example 1, the following compounds were prepared.

Reference Example 2

5-methyl-8-(3,4,5-trimethoxyphenyl)-1H-1,2,4-triazolo[5,1-i]purine (Melting point: 248–251° C.)

Reference Example 3

8-(4-biphenylyl)-5-methyl-1H-1,2,4-triazolo[5,1-i]purine (Melting point: 280° C. or higher)

Reference Example 4

5-methyl-8-(4-n-propoxyphenyl)-1H-1,2,4-triazolo[5,1-i]purine (Melting point: 280° C. or higher)

Reference Example 5

8-(4-t-butylphenyl)-5-methyl-1H-1,2,4-triazolo[5,1-i]purine (Melting point: 280° C. or higher)

Reference Example 6

8-(4-chlorophenyl)-5-methyl-1H-1,2,4-triazolo[5,1-i]purine (Melting point: 280° C. or higher)

Reference Example 7

5-methyl-8-(4-trifluoromethylphenyl)-1H-1,2,4-triazolo[5,1-i]purine (Melting point: 280° C. or higher)

Example 1

Preparation of 8-(4-biphenylyl)-5-ethoxymethyl-1H-1,2,4-triazolo[5,1-i]purine 5.0 g of the compound obtained in Reference Example 3 was added in a solution of concentrated hydrochloric acid (15 ml) in water (35 ml) and ethanol (25 ml), and the solution was heated at reflux for 24 hours. The reaction solution was air-cooled to room temperature and the pH of the solution was adjusted to 8 by adding an aqueous 25% ammonia water. The deposited crystal was collected by filtration and then purified by silica gel column chromatography (eluent: chloroform:methanol=30:1, then chloroform:methanol=10:1) to obtain 2.8 g of 3-(4-aminoimidazol-5-yl)-5-(4-biphenylyl)-1,2,4-triazole as a crystal (melting point: 230° C. or higher (with decomposition)).

To a solution of ethoxyacetic acid (0.6 g) in dichloromethane (10 ml), 0.4 ml of thionyl chloride was added and the solution was heated at reflux for one hour. After the resulting solution was cooled and added dropwise in a solution of the crystal (0.5 g) in pyridine (4 ml), the mixed solution was stirred at 0° C. for 30 minutes, then at room temperature for one hour, and heated at reflux for 1 hour. The reaction solution was concentrated under reduced pressure and the residue was dissolved in 40 ml of ethanol, and the solution was heated at reflux for 15 minutes. The reaction solution was cooled to room temperature, and then the deposited crystal was collected by filtration and sequentially washed with ethanol and 80% hot ethanol to obtain 0.51 g of 5-(4-biphenylyl)-3-[4-(N-ethoxyacetylamino)imidazol-5-yl]-1,2,4-triazole as a crystal (melting point: 280° C. or higher).

0.45 g of the resulting crystal was suspended in 5 ml of dichloromethane and, after adding 2 ml of diisopropylethylamine and 0.74 ml of chlorotrimethylsilane, the suspension was heated at reflux for 72 hours. The reaction solution was cooled to room temperature, diluted with chloroform, and then neutralized by adding hydrochloric acid. The deposited crystal was collected by filtration, washed with 50% hot ethanol and then air-dried to obtain 0.34 g of the objective compound as a crystal.

(Melting point: 280° C. or higher)

Examples 2 to 30

In the same manner as in Example 1, the following compounds were prepared.

Example 2

8-(4-biphenylyl)-5-methoxymethyl-1H-1,2,4-triazolo[5,1-i]purine (Melting point: 280° C. or higher)

Example 3

8-(4-biphenylyl)-5-(2-methoxyethyl)-1H-1,2,4-triazolo[5,1-i]purine (Melting point: 245 to 246° C.)

Example 4

8-(4-biphenylyl)-5-(2-methylthioethyl)-1H-1,2,4-triazolo[5,1-i]purine (Melting point: 249–251° C.)

Example 5

5-ethoxymethyl-8-(3,4,5-trimethoxyphenyl)-1H-1,2,4-triazolo[5,1-i]purine (Melting point: 254–255.5° C.)

Example 6

5-methoxymethyl-8-(3,4,5-trimethoxyphenyl)-1H-1,2,4-triazolo[5,1-i]purine (Melting point: 280° C. or higher)

Example 7

5-(2-methoxyethyl)-8-(3,4,5-trimethoxyphenyl)-1H-1,2,4-triazolo[5,1-i]purine(hydrate; water content=3.09%(w/w))

(Melting point: 192~194° C.)

Example 8

5-ethoxymethyl-8-(4-n-propoxyphenyl)-1H-1,2,4-triazolo[5,1-i]purine (Melting point: 262–263° C.)

Example 9

5-methoxymethyl-8-(4-n-propoxyphenyl)-1H-1,2,4-triazolo[5,1-i]purine (Melting point: 280° C. or higher)

Example 10

5-(2-methoxyethyl)-8-(4-n-propoxyphenyl)-1H-1,2,4-triazolo[5,1-i]purine (Melting point: 231.5–232.5° C.)

Example 11

5-ethoxymethyl-8-phenyl-1H-1,2,4-triazolo[5,1-i]purine (Melting point: 247–249° C.)

Example 12

5-methoxymethyl-8-phenyl-1H-1,2,4-triazolo[5,1-i]purine (Melting point: 280° C. or higher)

Example 13

5-(2-methoxyethyl)-8-phenyl-1H-1,2,4-triazolo[5,1-i]purine(hydrate; water content=2.73%(w/w))

(Melting point: 217.5–218.5° C.)

Example 14

8-(4-t-butylphenyl)-5-ethoxymethyl-1H-1,2,4-triazolo[5,1-i]purine (Melting point: 243–244° C.)

Example 15

8-(4-t-butylphenyl)-5-methoxymethyl-1H-1,2,4-triazolo[5,1-i]purine (Melting point: 280° C. or higher)

Example 16

8-(4-t-butylphenyl)-5-(2-methoxyethyl)-1H-1,2,4-triazolo[5,1-i]purine (Melting point: 237–239° C.)

Example 17

8-(4-t-butylphenyl)-5-(2-methylthioethyl)-1H-1,2,4-triazolo[5,1-i]purine (Melting point: 229–231° C.)

Example 18

5-(3-methoxycarbonylpropyl)-8-phenyl-1H-1,2,4-triazolo[5,1-i]purine (Melting point: 228–230° C.)

Example 19

5-(2-methylthioethyl)-8-(3,4,5-trimethoxyphenyl)-1H-1,2,4-triazolo[5,1-i]purine (Melting point: 233–234° C.)

Example 20

8-(4-biphenylyl)-5-(2-ethoxycarbonylethyl)-1H-1,2,4-triazolo[5,1-i]purine (Melting point: 241.5–244° C.)

Example 21

8-(4-biphenylyl)-5-(3-methoxycarbonylpropyl)-1H-1,2,4-triazolo[5,1-i]purine (Melting point: 243–245.5° C.)

Example 22

8-(4-biphenylyl)-5-(4-ethoxycarbonylbutyl)-1H-1,2,4-triazolo[5,1-i]purine (Melting point: 241–243° C.)

Example 23

8-(4-t-butylphenyl)-5-(3-methoxycarbonylpropyl)-
1H-1,2,4-triazolo[5,1-i]purine (Melting point: 169–172.5° C.)

Example 24

5-methoxymethyl-8-(4-trifluoromethylphenyl)-1H-1,
2,4-triazolo[5,1-i]purine (Melting point: 280° C. or higher)

Example 25

5-ethoxymethyl-8-(4-trifluoromethylphenyl)-1H-1,2,
4-triazolo[5,1-i]purine (Melting point: 280° C. or higher)

Example 26

5-(2-methoxyethyl)-8-(4-trifluoromethylphenyl)-1H-
1,2,4-triazolo[5,1-i]purine (Melting point: 256° C. or higher; with decomposition)

Example 27

5-(2-methylthioethyl)-8-(4-trifluoromethylphenyl)-
1H-1,2,4-triazolo[5,1-i]purine (Melting point: 255° C. or higher; with decomposition)

Example 28

8-(4-chlorophenyl)-5-(2-methoxyethyl)-1H-1,2,4-
triazolo[5,1-i]purine (Melting point: 278° C. or higher; with decomposition)

Example 29

8-(4-chlorophenyl)-5-(2-methylthioethyl)-1H-1,2,4-
triazolo[5,1-i]purine (Melting point: 257° C. or higher; with decomposition)

Example 30

8-(4-chlorophenyl)-5-(3-methoxycarbonylpropyl)-
1H-1,2,4-triazolo[5,1-i]purine (Melting point: 261–262.5° C.)

Example 31

Preparation of 5-(3-carboxypropyl)-8-phenyl-1H-1,
2,4-triazolo[5,1-i]purine 0.5 g of the compound obtained in Example 18 was suspended in 5 ml of ethanol and 1.78 ml of an aqueous 10% sodium hydroxide solution was added, followed by stirring at room temperature for 2 hours. The reaction solution was diluted with 40 ml of water and then acidified by adding hydrochloric acid. The deposited crystal was collected by filtration, sequentially washed with water and hot ethanol-water and then dried to obtain 0.35 g of the objective compound as a crystal (melting point: 280° C. or higher).

Examples 32 to 36

In the same manner as in Example 31, the following corresponding compounds were prepared from the compounds of Examples 20 to 23 and 30.

Example 32

8-(4-biphenylyl)-5-(2-carboxyethyl)-1H-1,2,4-
triazolo[5,1-i]purine (Melting point: 280° C. or higher)

Example 33

8-(4-biphenylyl)-5-(3-carboxypropyl)-1H-1,2,4-
triazolo[5,1-i]purine (Melting point: 280° C. or higher)

Example 34

8-(4-biphenylyl)-5-(4-carboxybutyl)-1H-1,2,4-
triazolo[5,1-i]purine (Melting point: 280° C. or higher)

Example 35

8-(4-t-butylphenyl)-5-(3-carboxypropyl)-1H-1,2,4-
triazolo[5,1-i]purine (Melting point: 280° C. or higher)

Example 36

5-(3-carboxypropyl)-8-(4-chlorophenyl)-1H-1,2,4-
triazolo[5,1-i]purine (Melting point: 280° C. or higher)

Example 37

Preparation of 8-(4-biphenylyl)-5-(2-
methylsulfinylethyl)-1H-1,2,4-triazolo[5,1-i]purine 0.15 g of the compound obtained in Example 4 was suspended in 1.5 ml of acetic acid and 50 µl of 30% hydrogen peroxide solution was added, followed by stirring at room temperature for 20 minutes. To the reaction solution, 3 ml of water was added. The deposited crystal was collected by filtration, sequentially washed with water and hot ethanol-water and then dried to obtain 0.14 g of the objective compound as a crystal. (Melting point: 188° C. or higher; with decomposition)

Examples 38 to 40

In the same manner as in Example 37, the following corresponding compounds were prepared from the compounds of Example 29, 17 and 27.

Example 38

8-(4-chlorophenyl)-5-(2-methylsulfinylethyl)-1H-1,
2,4-triazolo[5,1-i]purine (Melting point: 218° C. or higher; with decomposition)

Example 39

8-(4-t-butylphenyl)-5-(2-methylsulfinylethyl)-1H-1,
2,4-triazolo[5,1-i]purine (Melting point: 162° C. or higher; with decomposition)

Example 40

5-(2-methylsulfinylethyl)-8-(4-
trifluoromethylphenyl)-1H-1,2,4-triazolo[5,1-i]
purine (Melting point: 203° C. or higher; with decomposition)

Example 41

Preparation of 8-(4-biphenylyl)-5-(2-methylsulfonylethyl)-1H-1,2,4-triazolo[5,1-i]purine 0.25 g of the compound obtained in Example 4 was suspended in 5 ml of acetic acid and 0.16 ml of 30% hydrogen peroxide solution was added, followed by stirring at room temperature for 15 minutes and further stirring at 55° C. for 16 hours. After the completion of the reaction, the deposited crystal was collected by filtration, sequentially washed with water and hot ethanol-water and then dried to obtain 0.28 g of the objective compound as a crystal. (Melting point: 280° C. or higher)

Examples 42 to 44

In the same manner as in Example 41, the following corresponding compounds were prepared from the compounds of Examples 29, 17 and 27.

Example 42

8-(4-chlorophenyl)-5-(2-methylsulfonylethyl)-1H-1,2,4-triazolo[5,1-i]purine (Melting point: 244° C. or higher; with decomposition)

Example 43

8-(4-t-butylphenyl)-5-(2-methylsulfonylethyl)-1H-1,2,4-triazolo[5,1-i]purine (Melting point: 201° C. or higher; with decomposition)

Example 44

5-(2-methylsulfonylethyl)-8-(4-trifluoromethylphenyl)-1H-1,2,4-triazolo[5,1-i]purine (Melting point: 261° C. or higher; with decomposition)

Examples 45 to 59

In the same manner as in Example 1, the following compounds were prepared.

Example 45

8-(4-biphenylyl)-5-cyclohexyl-1H-1,2,4-triazolo[5,1-i]purine (Melting point: 280° C. or higher)

Example 46

8-(4-biphenylyl)-5-cyclopentyl-1H-1,2,4-triazolo[5,1-i]purine (Melting point: 280° C. or higher)

Example 47

8-(4-biphenylyl)-5-trifluoromethyl-1H-1,2,4-triazolo[5,1-i]purine (Melting point: 280° C. or higher)

Example 48

8-(4-biphenylyl)-5-methylthiomethyl-1H-1,2,4-triazolo[5,1-i]purine (Melting point: 284–286° C.)

Example 49

8-(4-biphenylyl)-5-ethylthiomethyl-1H-1,2,4-triazolo[5,1-i]purine (Melting point: 264–266° C.)

Example 50

8-(4-biphenylyl)-5-diethylphosphonomethyl-1H-1,2,4-triazolo[5,1-i]purine (Melting point: 188–192° C.)

Example 51

8-(4-biphenylyl)-5-(2-diethylphosphonoethyl)-1H-1,2,4-triazolo[5,1-i]purine (Melting point: 110° C. or higher)

Example 52

8-(4-biphenylyl)-5-acetoxymethyl-1H-1,2,4-triazolo[5,1-i]purine (Melting point: 233–235° C.)

Example 53

8-(4-t-butylphenyl)-5-diethylphosphonomethyl-1H-1,2,4-triazolo[5,1-i]purine (Melting point: 162–166° C.)

Example 54

8-(4-biphenylyl)-5-dimethylaminomethyl-1H-1,2,4-triazolo[5,1-i]purine (Melting point: 284–286° C.; with decomposition)

Example 55

8-(4-biphenylyl)-5-(3-dimethylaminopropyl)-1H-1,2,4-triazolo[5,1-i]purine (Melting point: 227–230° C.; with decomposition)

Example 56

5-(3-benzyloxypropyl)-8-(4-biphenylyl)-1H-1,2,4-triazolo[5,1-i]purine (Melting point: 237–238° C.)

Example 57

5-(4-benzyloxybutyl)-8-(4-biphenylyl)-1H-1,2,4-triazolo[5,1-i]purine (Melting point: 205–207° C.)

Example 58

5-diethylphosphonomethyl-8-(4-trifluoromethylphenyl)-1H-1,2,4-triazolo[5,1-i]purine (Melting point: 196–198° C.)

Example 59

8-(4-biphenylyl)-5-(3-diethylphosphonopropyl)-1H-1,2,4-triazolo[5,1-i]purine (Melting point: 175–178° C.)

Examples 60 to 61

In the same manner as in Example 37, the following corresponding compounds were prepared from the compounds of Example 48 and Example 49.

Example 60

8-(4-biphenylyl)-5-methylsulfinylmethyl-1H-1,2,4-triazolo[5,1-i]purine (Melting point: 246° C. or higher; with decomposition)

Example 61

8-(4-biphenylyl)-5-(2-methylsulfinylethyl)-1H-1,2,4-triazolo[5,1-i]purine (Melting point: 234° C. or higher; with decomposition)

Example 62

Preparation of 8-(4-biphenylyl)-5-hydroxymethyl-1H-1,2,4-triazolo[5,1-i]purine

The objective compound was obtained by subjecting the compound of Example 52 to the same reaction treatment as in Example 31. (Melting point: 280° C. or higher)

Example 63

Preparation of 8-(4-t-butylphenyl)-5-ethylphosphonomethyl-1H-1,2,4-triazolo[5,1-i]purine 0.20 g of the compound of Example 53 and 0.47 g of lithium bromide were suspended in 4 ml of acetonitrile, followed by stirring at 60° C. for 72 hours. After air-cooling the reaction mixture to room temperature, the deposited crystal was collected by filtration and washed twice with 10 ml of acetonitrile. The resulting crystal was dissolved in 10 ml of 50% ethanol and 0.45 ml of an aqueous 1N hydrochloric acid solution was added to the solution under stirring at room temperature. After stirring at room temperature for 10 minutes, the deposited crystal was collected by filtration and recrystallized from ethanol-water to obtain 0.12 g of the objective compound as a crystal (melting point: 254–256° C.)

Examples 64 and 65

In the same manner as in Example 63, the following corresponding compounds were prepared from the compounds of Examples 58 and Example 50.

Example 64

5-ethylphosphonomethyl-8-(4-trifluoromethylphenyl)-1H-1,2,4-triazolo[5,1-i]purine (Melting point: 268–270° C.)

Example 65

8-(4-biphenylyl)-5-ethylphosphonomethyl-1H-1,2,4-triazolo[5,1-i]purine (Melting point: 274–277° C.)

Example 66

Preparation of 8-(4-t-butylphenyl)-5-phosphonomethyl-1H-1,2,4-triazolo[5,1-i]purine 0.20 g of the compound of Example 53 and 0.20 g of sodium iodide were suspended in 4 ml of acetonitrile and 0.17 ml of chlorotrimethylsilane was slowly added dropwise in the suspension at room temperature. After stirring at room temperature for 3 hours and further stirring at 50° C. for 20 hours, 10 ml of water was added in the reaction mixed solution and the solution was heated at reflux for 10 minutes. After cooling to room temperature, the deposited crystal was collected by filtration and washed with hot ethanol to obtain 0.10 g of the objective compound as a crystal. (Melting point: 270° C. or higher; with decomposition)

With respect to the compounds of the Examples described above, $^1$H-NMR spectrum data($\delta$: ppm) are shown below. Dimethyl sulfoxide-d6 was used as a measuring solvent and tetramethylsilane was used as an internal standard.

Example 1

1.30(3H,t,J=6.9),3.85(2H,q,J=6.9),5.20(2H,s),7.4–7.7(3H,m),7.84(2H,d,J=8.2),7.95(2H,d,J=8.2),8.42(2H,d,J=8.2),8.56(1H,s).

Example 2

3.54(3H,s),5.11(2H,s),7.4–7.6(3H,m),7.79(2H,d,J=7.2), 7.91(2H,d,J=8.4), 8.38(2H,d,J=8.4),8.50(1H,s).

Example 3

3.38(3H,s),3.70(2H,t,J=6.4),4.08(2H,t,J=6.4), 7.4–7.7(3H,m), 7.84(2H,d,J=7.9), 7.95(2H,d,J=8.2),8.42(2H,d,J=8.2),8.51(1H, s).

Example 4

2.20(3H,s),3.15(2H,t,J=7.2),3.69(2H,t,J=7.2), 7.4–7.6(3H,m), 7.78(2H,d,J=7.4), 7.90(2H,d,J=8.2),8.37(2H,d,J=8.2),8.46(1H, s).

Example 5

1.24(3H,t,J=6.9),3.77(3H,s), 3.78(2H,q,J=6.9),3.93(6H,s),5.14(2H,s),7.56(2H,s), 8.49(1H,s).

Example 6

3.53(3H,s), 3.76(3H,s),3.93(6H,s),5.10(2H,s),7.56(2H,s), 8.49(1H,s).

Example 7

3.31(3H,s),3.64(2H,t,J=6.4),3.77(3H,s),3.93(6H,s), 4.01(2H, t,J=6.4), 7.56(2H,s), 8.44(1H,s).

Example 8

1.01(3H,t,J=7.4),1.22(3H,t,J=6.9)1.7–1.9(2H,m),3.76(2H,q,J=6.9), 4.03(2H,t,J=6.9),5.11(2H,s), 7.12(2H,d,J=8.9),8.20(2H, d,J=8.9),8.47(1H,s).

Example 9

1.01(3H,t,J=7.4),1.7–1.9(2H,m),3.52(3H,s),4.03(2H,t,J=6.4), 5.07(2H,s),7.12(2H,d,J=8.9),8.20(2H,d,J=8.9),8.48(1H,s).

Example 10

1.10(3H,t,J=7.4),1.8–2.0(2H,m),3.39(3H,s),3.69(2H,t,J=6.4), 4.0–4.2(4H,m), 7.20(2H,d,J=8.9), 8.28(2H,d,J=8.9), 8.51(1H, s).

Example 11

1.23(3H,t,J=6.9),3.77(2H,q,J=6.9),5.13(2H,s),7.5–7.6(3H,m), 8.2–8.3(2H,m), 8.49(1H,s).

Example 12

3.53(3H,s),5.10(2H,s),7.5–7.6(3H,m),8.2–8.3(2H,m), 8.50(1H, s).

Example 13

3.31(3H,s),3.64(2H,t,J=6.4),4.01(2H,t,J=6.4),7.5–7.6 (3H,m), 8.2–8.3(2H,m), 8.45(1H,s),13.6–14.1(1H,brs).

Example 14

1.22(3H,t,J=7.4),1.35(9H,s),3.77(2H,q,J=7.4),5.12(2H,s), 7.61(2H,d,J=8.4), 8.21(2H,d,J=8.4),8.49(1H,s).

Example 15

1.42(9H,s),3.60(3H,s),5.16(2H,s),7.67(2H,d,J=8.4),8.29 (2H,d, J=8.4),8.56(1H,s).

Example 16

1.35(9H,s),3.30(3H,s),3.63(2H,t,J=6.4),4.00(2H,t,J=6.4), 7.60(2H,d,J=8.4), 8.21(2H,d,J=8.4),8.44(1H,s),13.6–14.1 (1H,br s).

Example 17

1.35(9H,s),2.18(3H,s),3.13(2H,t,J=7.4),3.67(2H,t,J=7.4), 7.60(2H,d,J=8.4), 8.21(2H,d,J=8.4),8.45(1H,s),13.7–14.0 (1H,br s).

Example 18

2.2–2.4(2H,m),2.65(2H,t,J=7.4),3.49(2H,t,J=7.4),3.65 (3H,s), 7.6–7.7(3H,m), 8.3–8.4(2H,m),8.51(1H,s).

Example 19

2.20(3H,s),3.13(2H,t,J=7.4),3.67(2H,t,J=7.4),3.76(3H,s), 3.92(6H,s),7.56(2H,s),8.45(1H,s).

Example 20

1.26(3H,t,J=7.4),3.14(2H,t,J=6.9),3.74(2H,t,J=6.9),4.17 (2H, q,J=7.4),7.5–7.7(3H,m),7.87(2H,d,J=7.9),7.98(2H,d, J=8.4),8.46(2H,d,J=8.4),8.52(1H,s).

Example 21

2.2–2.3(2H,m),2.57(2H,t,J=6.9),3.42(2H,t,J=7.4),3.58 (3H,s), 7.4–7.6(3H,m), 7.78(2H,d,J=6.9),7.89(2H,d,J=8.4), 8.36(2H,d, J=8.4),8.44(1H,s).

Example 22

1.24(3H,t,J=6.9),1.7–1.9(2H,m),2.0–2.2(2H,m),2.49(2H, t,J=7.4),3.46(2H,t,J=7.4), 4.12(2H,q,J=6.9),7.4–7.6(3H,m), 7.85(2H, d,J=6.9),7.96(2H,d,J=8.4), 8.44(2H,d,J=8.4),8.51 (1H,s).

Example 23

1.43(9H,s),2.2–2.4(2H,m),2.64(2H,t,J=7.4),3.48(2H,t,J= 7.4), 3.65(3H,s),7.68(2H,d,J=8.4),8.29(2H,d,J=8.4),8.50 (1H,s).

Example 24

3.54(3H,s),5.11(2H,s),7.96(2H,d,J=8.4),8.48(2H,d,J= 8.4),8.52(1H,s).

Example 25

1.23(3H,t,J=6.9),3.77(2H,q,J=6.9),5.14(2H,s),7.96(2H,d, J=8.4),8.49(2H,d,J=8.4), 8.51(1H,s).

Example 26

3.31(3H,s),3.64(2H,t,J=6.4),4.01(2H,t,J=6.4),7.95(2H,d, J=8.4),8.47(1H,s),8.48(2H,d,J=8.4).

Example 27

2.19(3H,s),3.14(2H,t,J=7.4),3.68(2H,t,J=7.4),7.95(2H,d, J=8.4),8.47(1H,s),8.49(2H,d,J=8.4).

Example 28

3.31(3H,s),3.62(2H,t,J=6.4),4.00(2H,t,J=6.4),7.64(2H,d, J=8.4),8.27(2H,d,J=8.4), 8.45(1H,s).

Example 29

2.18(3H,s),3.13(2H,t,J=7.4),3.66(2H,t,J=7.4),7.64(2H,d, J=8.4),8.28(2H,d,J=8.4), 8.46(1H,s).

Example 30

2.1–2.3(2H,m),2.56(2H,t,J=7.4),3.39(2H,t,J=7.4),7.64 (2H,d,J=8.9), 8.27(2H,d,J=8.9),8.43(1H,s).

Example 31

2.1–2.3(2H,m),2.47(2H,t,J=6.9),3.41(2H,t,J=7.4),7.5–7.6 (3H, m),8.2–8.3(2H, m),8.43(1H,s).

Example 32

3.07(2H,t,J=6.9),3.70(2H,t,J=6.9),7.4–7.6(3H,m),7.86 (2H,d,J=7.4), 7.97(2H,d,J=8.4),8.45(2H,d,J=8.4),8.52(1H, s).

Example 33

2.1–2.3(2H,m),2.48(2H,t,J=6.9),3.42(2H,t,J=6.8),7.4–7.6 (3H, m), 7.78(2H,d,J=7.4),7.89(2H,d,J=8.4),8.37(2H,d,J= 8.4),8.44(1H,s).

Example 34

1.6–1.8(2H,m),1.9–2.1(2H,m),2.34(2H,t,J=7.4),3.39(2H, t,J=7.9),7.4–7.6(3H,m),7.78(2H,d,J=7.9),7.89(2H,d,J=8.4), 8.37(2H, d,J=8.4),8.43(1H,s).

Example 35

1.35(9H,s),2.1–2.3(2H,m),2.47(2H,t,J=6.9),3.40(2H,t,J= 7.4), 7.60(2H,d,J=8.4),8.21(2H,d,J=8.4),8.43(1H,s).

Example 36

2.1–2.3(2H,m),2.46(2H,t,J=6.9),3.40(2H,d,J=7.4),7.64 (2H,d,J=8.4),8.28(2H,d,J=8.4),8.43(1H,s).

Example 37

2.70(3H,s),3.2–3.6(2H,m),3.79(2H,t,J=6.9),7.4–7.6(3H, m),7.78(2H,d,J=7.4), 7.90(2H,d,J=8.4),8.38(2H,d,J=8.4), 8.47(1H, s).

Example 38

2.69(3H,s),3.2–3.6(2H,m),3.76(2H,t,J=7.4),7.64(2H,d,J= 8.4), 8.29(2H,d,J=8.4),8.46(1H,s)

Example 39

1.35(9H,s),2.69(3H,s),3.2–3.6(2H,m),3.77(2H,t,J=7.4), 7.60(2H,d,J=8.4),8.22(2H,d,J=8.4),8.45(1H,s).

Example 40

2.70(3H,s),3.2–3.6(2H,m),3.78(2H,t,J=7.9),7.95(2H,d,J= 8.4), 8.48(1H,s), 8.49(2H,d,J=8.4).

Example 41

3.18(3H,s),3.86(4H,s),7.4–7.6(3H,m),7.78(2H,d,J=7.4),7.90(2H,d,J=8.4),8.39(2H,d,J=8.4),8.48(1H,s).

Example 42

3.16(3H,s),3.83(4H,s),7.65(2H,d,J=8.4),8.31(2H,d,J=8.4),8.48(1H,s).

Example 43

1.35(9H,s),3.17(3H,s),3.84(3H,s),7.61(2H,d,J=8.4),8.23(2H,d, J=8.4),8.47(1H,s).

Example 44

3.17(3H,s),3.85(4H,s),7.96(2H,d,J=8.4),8.49(1H,s),8.51(2H,d, J=8.4).

Example 45

1.3–2.0(8H,m),2.1–2.3(2H,m),3.7–3.8(1H,m),7.4–7.6(3H,m),7.79(2H,d,J=7.4),7.91(2H,d,J=8.4),8.38(2H,d,J=8.4),8.45(1H,s).

Example 46

1.7–1.9(4H,m),2.0–2.1(2H,m),2.2–2.3(2H,m),4.15(1H,quint,J=7.9),7.4–7.6(3H,m),7.78(2H,d,J=7.9),7.90(2H,d,J=8.4),8.37(2H, d,J=8.4),8.43(1H,s),13.6–14.1(1H,brs).

Example 47

7.4–7.6(3H,m),7.79(2H,d,J=6.9),7.93(2H,d,J=8.4),8.38(2H,d,J=8.4),8.73(1H,s).

Example 48

2.26(3H,s),4.38(2H,s),7.4–7.6(3H,m),7.78(2H,d,J=6.9),7.90(2H,d,J=8.4),8.37(2H,d,J=8.4),8.49(1H,s).

Example 49

1.27(3H,t,J=7.4),2.72(2H,q,J=7.4),4.41(2H,s),7.4–7.6(3H,m), 7.78(2H,d,J=7.4),7.90(2H,d,J=8.4),8.36(2H,d,J=8.4),8.49(1H, s).

Example 50

1.19(6H,t,J=6.9),4.0–4.2(6H,m),7.4–7.6(3H,m),7.79(2H,d,J=7.2),7.91(2H,d,J=8.4),8.38(2H,d,J=8.4),8.50(1H,s).

Example 51

1.24(6H,t,J=6.9),2.4–2.5(2H,m),3.5–3.6(2H,m),4.0–4.1(4H,m), 7.4–7.6(3H,m),7.78(2H,d,J=7.4),7.90(2H,d,J=8.4),8.37(2H,d,J=8.4),8.47(1H,s).

Example 52

2.22(3H,s),5.76(2H,s),7.4–7.6(3H,m),7.78(2H,d,J=7.2),7.90(2H,d,J=8.4),8.37(2H,d,J=8.4),8.52(1H,s).

Example 53

1.18(6H,t,J=7.4),1.35(9H,s),4.0–4.2(6H,m),7.62(2H,d,J=8.7), 8.22(2H,d,J=8.7),8.48(1H,s).

Example 54

2.43(6H,s),4.20(2H,s),7.4–7.6(3H,m),7.78(2H,d,J=7.2),7.90(2H,d,J=8.4),8.37(2H,d,J=8.4),8.48(1H,s).

Example 55

2.0–2.2(2H,m),2.18(6H,s),2.43(2H,t,J=6.9),3.39(2H,t,J=7.2), 7.4–7.6(3H,m),7.78(2H,d,J=8.2),7.89(2H,d,J=8.4),8.36(2H,d,J=8.4),8.42(1H,s).

Example 56

2.2–2.3(2H,m),3.48(2H,t,J=7.2),3.65(2H,t,J=6.2),4.48(2H,s), 7.2–7.6(8H,m),7.78(2H,d,J=7.2),7.89(2H,d,J=8.4),8.37(2H,d,J=8.4),8.43(1H,s).

Example 57

1.7–1.8(2H,m),1.9–2.2(2H,m),3.41(2H,t,J=7.4),3.54(2H,t,J=6.2),4.47(2H,s),7.2–7.6(8H,m),7.78(2H,d,J=8.2),7.88(2H,d,J=8.4),8.36(2H,d,J=8.4),8.43(1H,s).

Example 58

1.18(6H,t,J=6.9),4.0–4.2(6H,m),7.98(2H,d,J=8.4),8.50(2H,d,J=8.4),8.51(1H,s).

Example 59

1.24(6H,t,J=6.9),1.9–2.1(2H,m),2.1–2.3(2H,m),3.50(2H,t,J=7.4),3.94.1(4H,m),7.4–7.6(3H,m),7.78(2H,d,J=7.4),7.90(2H,d,J=8.4),8.37(2H,d,J=8.4),8.44(1H,s).

Example 60

2.88(3H,s),4.84(1H,d,J=13.4),5.00(1H,d,J=13.4),7.4–7.6(3H, m),7.79(2H,d,J=7.4),7.91(2H,d,J=8.4),8.39(2H,d,J=8.4),8.53 (1H,s).

Example 61

1.33(3H,t,J=7.4),2.9–3.2(2H,m),4.78(1H,d,J=13.4),4.97(1H,d, J=13.4),7.4–7.6(3H,m),7.79(2H,d,J=7.9),7.91(2H,d,J=8.4),8.38(2H,d,J=8.4),8.53(1H,s).

Example 62

5.13(2H,s),5.79(1H,brs),7.4–7.6(3H,m),7.79(2H,d,J=8.2),7.90 (2H,d,J=8.2),8.38(2H,d,J=8.2),8.48(1H,s).

Example 63

1.16(3H,t,J=7.2),1.35(9H,s),3.9–4.1(4H,m),7.61(2H,d,J=8.2), 8.22(2H,d,J=8.2),8.46(1H,s).

Example 64

1.16(3H,t,J=6.9),3.9–4.1(4H,m),7.97(2H,d,J=8.4),8.49(1H,s), 8.50(2H,d,J=8.4).

Example 65

1.18(3H,t,J=6.9),3.9–4.2(4H,m),7.4–7.6(3H,m),7.78(2H,d,J=7.9),7.90(2H,d,J=8.4),8.37(2H,d,J=8.4),8.48(1H,s).

Example 66

1.38(9H,s),3.8–4.1(2H,m),7.60(2H,d,J=8.4),8.21(2H,d,J=8.4), 8.45(1H,brs).

Experiment

Adenosine A3 Receptor Binding Capacity Test of Triazolopurine Derivative (1)

According to the method described in Molecular Pharmacology, 45, 978 (1994), an adenosine A3 receptor binding capacity test was performed.

A cell membrane of human renal endothelial cells HEK-293 transformed with plasmid coding an adenosine A3 receptor was isolated in a Tris-hydrochloric acid buffer (pH 7.7) in accordance with a conventional method, and then the cell membrane was treated with $N^6$-(4-aminobenzyl)-9-[5-(methylcarbonyl)-β-D-ribofuranosyl]adenine (AB-MECA) labelled with $^{125}I$ to prepare a cell membrane bound with the compound.

Then, this cell membrane and a test compound were incubated and the amount of [$^{125}$I]AB-MECA liberated was measured. The concentration of the test compound when 50% of [$^{125}$I]AB-MECA is liberated, $IC_{50}$ was determined from the measured value of the test compound at each concentration.

The adenosine A2 receptor binding capacity of the test compound was measured according to the method described in Archives of Pharmacology, 336, 204 (1987) and The Journal of Pharmacology and Experimental Therapeutics, 251 (3), 888 (1989) and then evaluated as $IC_{50}$. The measurement results are shown in the following tables.

TABLE 1

| Example No. | Receptor binding capacity ($IC_{50}$) (nM) | |
|---|---|---|
| | Adenosine A2 | Adenosine A3 |
| 3 | $\geq 1 \times 10^4$ | 0.9 |
| 4 | $\geq 1 \times 10^4$ | 1.1 |
| 5 | $\geq 1 \times 10^4$ | 24 |
| 6 | $\geq 1 \times 10^4$ | 104 |
| 7 | $\geq 1 \times 10^4$ | 27 |
| 10 | 2821 | 0.9 |
| 11 | 827 | 1.6 |
| 12 | 792 | 2.2 |
| 13 | 1110 | 0.9 |
| 16 | $\geq 1 \times 10^4$ | 2.1 |
| 17 | $\geq 1 \times 10^4$ | 27 |
| 19 | 2544 | 5.6 |
| 26 | $\geq 1 \times 10^4$ | 2.4 |
| 27 | 3842 | 13 |
| 28 | 1097 | 0.9 |
| 29 | 670 | 1.1 |
| 32 | $\geq 1 \times 10^4$ | 14.5 |
| 33 | $\geq 1 \times 10^4$ | 8.7 |
| 34 | $\geq 1 \times 10^4$ | 9.1 |
| 37 | $\geq 1 \times 10^4$ | 5.6 |
| 41 | $\geq 1 \times 10^4$ | 2.6 |

Preparation Example 1

Preparation of Tablets

Two-thousands tablets, each of which contains 300 mg of the compound (8-(4-biphenylyl)-5-(2-methoxyethyl)-1H-1,2,4-triazolo[5,1-i]purine) obtained in Example 3 as an active ingredient, were prepared according to the following formulation.

| | |
|---|---|
| Compound obtained in Example 3 | 600 g |
| Lactose (Japanese Pharmacopoeia) | 67 g |
| Cornstarch (Japanese Pharmacopoeia) | 33 g |
| Calcium carboxymethylcellulose (Japanese Pharmacopoeia) | 25 g |
| Methylcellulose (Japanese Pharmacopoeia) | 12 g |
| Magnesium stearate (Japanese Pharmacopoeia) | 3 g |

According to the formulation described above, objective tablets were obtained by sufficiently mixing the compound obtained in Example 3, lactose, cornstarch and calcium carboxymethylcellulose, granulating the resulting mixture using an aqueous methylcellulose, passing the granules through a #24 mesh sieve, admixing the granules with magnesium stearate and compressing the admixture into tablets.

Preparation Example 2

Preparation of Capsules

Two-thousands hard gelatin capsules, each of which contains 200 mg of the compound (8-(4-biphenylyl)-5-(2-methylthioethyl)-1H-1,2,4-triazolo[5,1-i]purine) obtained in Example 4 as an active ingredient, were prepared according to the following formulation.

| | |
|---|---|
| Compound obtained in Example 4 | 400 g |
| Crystalline cellulose (Japanese Pharmacopoeia) | 60 g |
| Cornstarch (Japanese Pharmacopoeia) | 34 g |
| Talc (Japanese Pharmacopoeia) | 4 g |
| Magnesium stearate (Japanese Pharmacopoeia) | 2 g |

According to the formulation described above, objective capsules were obtained by pulverizing the respective ingredients to form powders, mixing the powders to obtain an uniform mixture and filling a gelatin capsule for oral administration having a desired size with the mixture.

What is claimed is:

1. A triazolopurine derivative represented by formula (1):

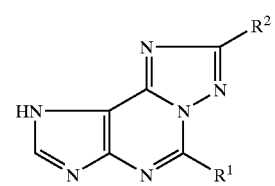

(1)

wherein $R^1$ represents a lower alkoxy lower alkyl group, a lower alkylsulfinyl lower alkyl group, a lower alkylsulfonyl lower alkyl group, a lower alkoxycarbonyl lower alkyl group, a carboxy lower alkyl group, a cycloalkyl group, a halogen-substituted lower alkyl group, a phosphono lower alkyl group, a lower alkylphosphono lower alkyl group, a di-lower alkylphosphono lower alkyl group, a lower alkanoyloxy lower alkyl group, a hydroxy lower alkyl group, a di-lower alkylamino lower alkyl group, a phenyl lower alkoxy lower alkyl group, or a lower alkylthio lower alkyl group; $R^2$ represents a phenyl group which optionally has, as a substituent, 1 to 3 groups selected from the group consisting of lower alkyl group, lower alkoxy group, halogen atom, halogen-substituted lower alkyl group, and phenyl group.

2. The triazolopurine derivative according to claim 1, wherein $R^1$ is a lower alkoxy lower alkyl group, a lower alkylsulfinyl lower alkyl group, a lower alkylsulfonyl lower alkyl group, a carboxy lower alkyl group, or a lower alkylthio lower alkyl group.

3. The triazolopurine derivative according to claim 1 or 2, wherein $R^1$ is a methoxymethyl group, an ethoxymethyl group, a 2-methoxyethyl group, a 2-methylsulfinylethyl group, a 2-methylsulfonylethyl group, a 2-carboxyethyl group, a 3-carboxypropyl group, a 4-carboxybutyl group, or a 2-methylthioethyl group.

4. The triazolopurine derivative according to claim 1, wherein $R^2$ is a phenyl group, a 4-biphenylyl group, a 4-n-propoxyphenyl group, a 4-t-butylphenyl group, a 4-chlorophenyl group, a 4-trifluoromethylphenyl group, or a 3,4,5-trimethoxyphenyl group.

5. The triazolopurine derivative according to claim 2, wherein $R^1$ is a lower alkoxy lower alkyl group or a lower alkylthio lower alkyl group, and $R^2$ is a biphenylyl group.

6. The triazolopurine derivative according to claim 5, wherein $R^1$ is a 2-methoxyethyl group or a 2-methylthiomethyl group and $R^2$ is a 4-biphenylyl group.

7. A pharmaceutical composition comprising the triazolopurine derivative of claim 1 and a pharmaceutically acceptable carrier.

8. A method of blocking or stimulating an adenosine A3 receptor, which comprises administering an effective amount of the triazolopurine derivative of claim 1.

* * * * *